(12) United States Patent
Lucas et al.

(10) Patent No.: US 6,841,565 B1
(45) Date of Patent: Jan. 11, 2005

(54) TREATMENT OF PATIENTS WITH CHRONIC LYMPHOCYTIC LEUKEMIA

(75) Inventors: David M. Lucas, Hilliard, OH (US); Mark R. Parthun, Hilliard, OH (US); John C. Byrd, Columbus, OH (US); Michael R. Grever, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 10/403,667

(22) Filed: Mar. 31, 2003

Related U.S. Application Data

(60) Provisional application No. 60/368,775, filed on Mar. 29, 2002.

(51) Int. Cl.$^7$ ............................................. A61K 31/44
(52) U.S. Cl. ........................ 514/346; 514/352; 514/357
(58) Field of Search ................................ 514/346, 352, 514/357

(56) References Cited

U.S. PATENT DOCUMENTS

| | | | | |
|---|---|---|---|---|
| 6,129,914 A | * | 10/2000 | Weiner et al. | 424/133.1 |
| 6,174,905 B1 | * | 1/2001 | Suzuki et al. | 514/346 |
| 6,316,435 B2 | * | 11/2001 | Byrd et al. | 514/211.08 |
| 6,320,078 B1 | * | 11/2001 | Suzuki et al. | 564/163 |

FOREIGN PATENT DOCUMENTS

| JP | 2002 256194 | 9/2000 |
|---|---|---|

OTHER PUBLICATIONS

Database BIOSIS on STN, AN 2002:367448, Lucas et al., "MS–275 reduces viability and induces change in histone acetylation in cells from patients with B–cell chronic lymphocytic leukemia", Proceedings of the American Associate for Cancer Research Annual Meeting, Mar. 2002, vol. 43, pp 69, meeting abstract.

Database BIOSIS on STN, AN 2003:336100, Lucas et al., "MS–275 promotes apoptosis in cell from patient with B–cell chronic lymphocytic leukemia (B –CLL) concurrent with inhibition of histone deactylase", Blood (2002) vol. 100k, No. 11, pp. Abstract No. 1500.

* cited by examiner

*Primary Examiner*—Raymond J. Henley, III
(74) *Attorney, Agent, or Firm*—Calfee, Halter & Griswold LLP

(57) ABSTRACT

The invention provides methods for treating a patient with chronic lymphocytic leukemia of B cells (B-CLL). One method comprises administering to a patient with B-CLL, one or more benzamide derivatives, the benzamide derivatives including MS-275 and related compounds. Another method comprises administering to a patient with B-CLL, one or more of the benzamide derivatives, and additionally administering to the patient one or more antibodies immunospecific for 1D10 antigen. Additional methods for inducing apoptosis of B-CLL cells and for increasing expression of 1D10 antigen in B-CLL cells using the benzamide derivatives are also provided.

8 Claims, 4 Drawing Sheets

TREATMENT OF PATIENTS WITH CHRONIC LYMPHOCYTIC LEUKEMIA

This application claims priority from U.S. Provisional Patent Application Ser. No. 60/368,775, filed on Mar. 29, 2002, which is incorporated herein by reference.

This invention was made, at least in part, with government support under National Institutes of Health Grant 2P01 CA81534. The U.S. government has certain rights in the invention.

FIELD OF THE INVENTION

This invention relates to methods for treating a patient with B cell chronic lymphocytic leukemia (B-CLL) by administering agents comprising benzamide derivatives such as MS-275, and optionally, additionally administering antibodies immunospecific for the 1D10 antigen to the patient.

BACKGROUND

Chronic lymphocytic leukemia (CLL) of B cells (B-CLL) is the most common type of adult leukemia. One in four human leukemias are of this type. In B-CLL, B cells are halted in their normal differentiation process and, therefore, are incapable of performing a variety of normal functions, and are resistant to normal programmed cell death. These B cells, herein called B-CLL cells, are malignant and accumulate in the blood of patients during the disease. Although the cells are not found to be undergoing DNA synthesis or mitosis, they accumulate in the blood of the B-CLL patient over a long period of time, often years. Accumulation of these inactive, non-proliferating B-CLL cells interferes with normal immune function in the patient, resulting in potentially fatal cytopenias and infections.

Accepted treatment regimens for patients with B-CLL consist of administration of a variety of therapeutic anti-CLL agents, including nucleoside analogs or alkylating agents, and current trials are investigating the benefits of combinations of these agents with monoclonal antibodies. However, therapeutic options for patients with B-CLL are limited, and in most cases, are ineffective or have a limited period of effectiveness. Relapse of the disease often occurs and these patients acquire resistance, not only to the drug used for patient treatment, but to other drugs as well.

Given these factors, discovery of new therapies and therapeutic combinations is critical in order to make significant progress in improving overall patient condition and survival in this disease.

SUMMARY OF THE INVENTION

The present invention provides methods for treating a patient suspected of having or known to have chronic lymphocytic leukemia (CLL) of B cells (B-CLL). One method comprises administering to a patient, a biologically effective amount of one or more compounds of the structures as pictured in I, II or III below:

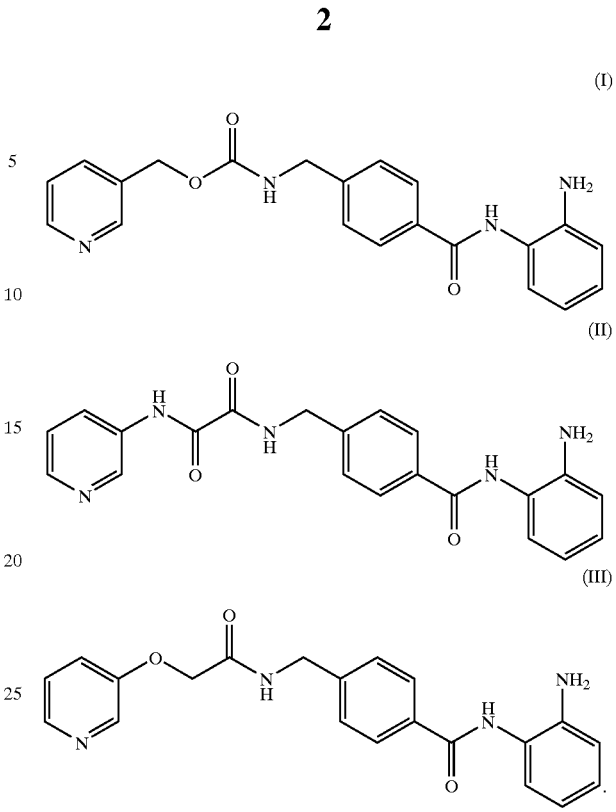

Another method comprises administering to a patient a biologically effective amount of one or more of the compounds of the structures as pictured in I, II or III above, and administering a biologically effective amount of one or more antibodies immunospecific for 1D10 antigen. The invention also provides methods for inducing apoptosis of B-CLL cells by contacting the cells with the compounds of the structures as pictured in I, II or III above. The invention also provides methods for inducing or increasing expression of 1D10 antigen on B-CLL cells by contacting the cells with the compounds of the structures as pictured in I, II or III above.

DETAILED DESCRIPTION OF THE INVENTION

Figure 1:
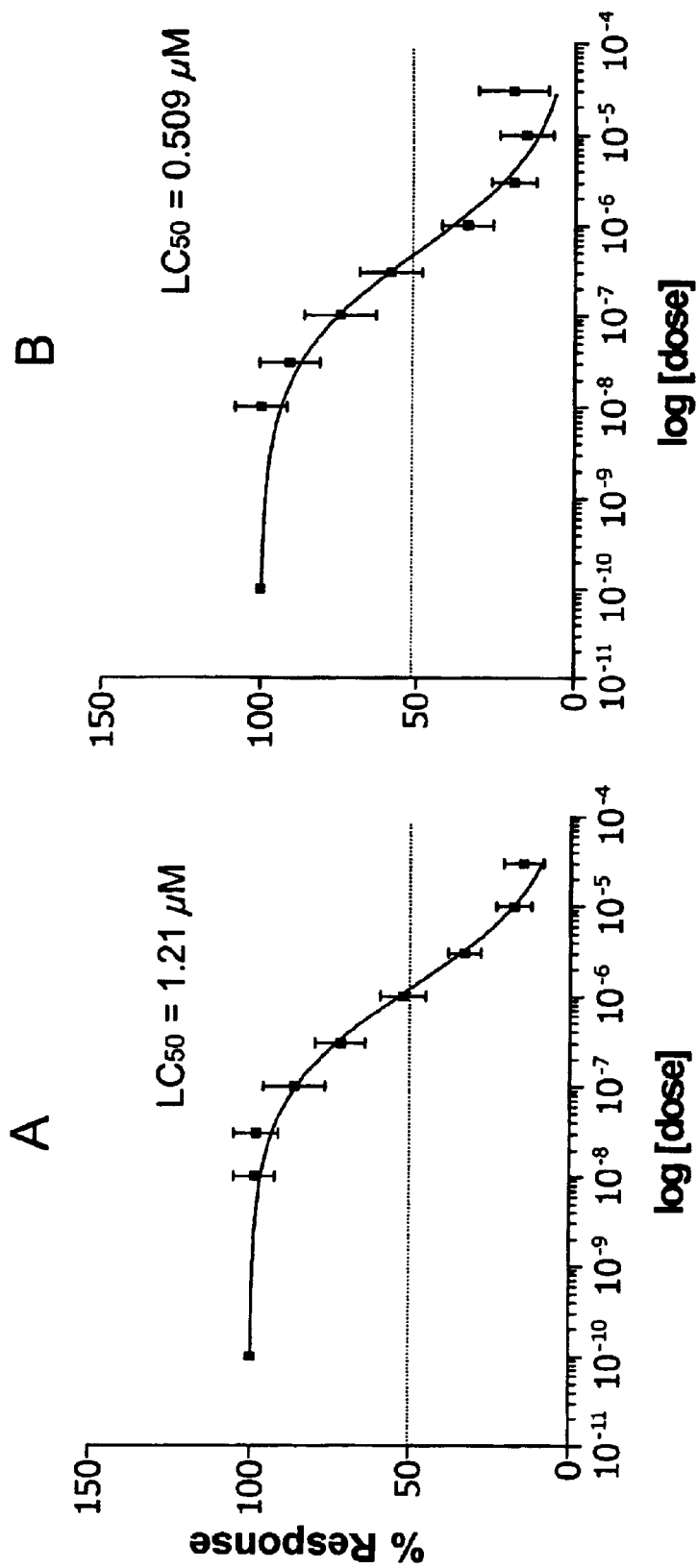
FIG. 1. $LC_{50}$ determination of MS-275 in primary B-CLL cells. Peripheral blood mononuclear cells (PBMCs) from thirteen individual B-CLL patients were isolated and incubated with varying concentrations of MS-275 from 0.01 to 100 uM. A. Cells were incubated in drug for 4 hours and were then washed and re-incubated in fresh media for a total of 96 hours. B. Cells were incubated in drug for 96 hours continuously. Viability was determined by an MTT assay to detect metabolic activity. Each patient sample at each concentration was run in quadruplicate and was normalized to cells from the same patient incubated for the same time period in media alone. Error bars represent 95% confidence intervals.

The malignant cells from patients with B cell chronic lymphocytic leukemia (B-CLL) are herein called B-CLL cells. These malignant B-CLL cells are halted in their normal differentiation process and are not found to be undergoing DNA synthesis or mitosis. These cells express relatively low levels of 1D10 antigen.

We have found that the compound MS-275, also called MS-27-275 or N-(2-aminophenyl)-4-[N-(pyridin-3-yl-methoxycarbonyl)aminomethyl]benzamide, is selectively toxic to B-CLL cells from patients with B-CLL compared to cells in peripheral blood mononuclear cell (PBMC) preparations from individuals who do not have B-CLL (normal individuals). We have found that the selective toxicity of MS-275 for B-CLL cells is due, at least in part, to induction of apoptosis of the B-CLL cells. We have also found that MS-275 induces increased expression of 1D10 antigen on the surface of B-CLL cells. Therapeutic antibodies exist that specifically bind to or are immunospecific for the 1D10 antigen.

Based on these findings, the present invention provides for methods of treating a patient who has B-CLL. In one embodiment, the method comprises administering a biologically effective amount of one or more benzamide derivatives to a patient that comprise the general chemical structure below, shown as IV:

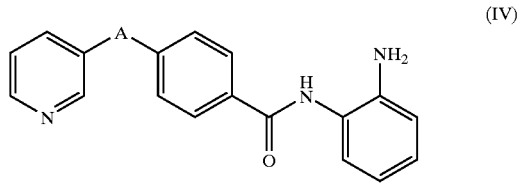
(IV)

wherein A represents a structure shown by either of the formulas V, VI or VII:

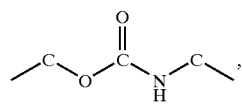
(V)

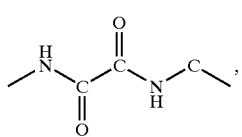
(VI)

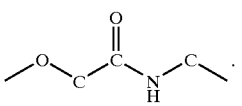
(VII)

In another embodiment, the method comprises administering a biologically effective amount of one or more of the above-described benzamide derivatives to a patient and administering a biologically effective amount of one or more antibodies immunospecific for 1D10 antigen to the patient.

MS-275 and Related Compounds

MS-275 is a synthetic benzamide derivative that has been shown to inhibit cellular histone deacetylase activity and to block growth in a variety of human tumor cell lines (A. Saito, et al., 1999, Proc. Natl. Acad. Sci. USA, A synthetic inhibitor of histone deacetylase, MS-27-275, with marked in vivo antitumor activity against human tumors, 96:4592–7). The chemical structure of MS-275 is shown as structure I in the Summary of the Invention section of this application. MS-275 is chemically synthesized using methods known in the art. One such method is described in T. Suzuki et al., 1999, J. Med. Chem., Synthesis and histone deacetylase inhibitory activity of new benzamide derivatives, 42:3001–3. Additional information relating to synthesis of MS-275 and related compounds is found in Japanese Unexamined Patent Publication Hei No. 10-152462. MS-275 is also available from various sources. One such source is Nihon Schering K.K. Another source is the National Cancer Institute (MS-275 is NSC No. 706995). Two benzamide derivatives closely related to MS-275 are shown as structures II and III in the Summary of the Invention section of this application.

In addition to the benzamide derivative compounds shown as structures I, II and III in the Summary of the Invention section of this application, pharmaceutically acceptable salts of the benzamide derivatives may be used in practice of the invention. Such salts include salts with an inorganic acid such as hydrochloric acid, hydrobromic acid, sulfuric acid and phosphoric acid; and with an organic acid such as acetic acid, lactic acid, tartaric acid, malic acid, succinic acid, fumaric acid, maleic acid, citric acid, benzoic acid, trifluroacetic acid, p-toluenesulfonic acid and methanesulfonic acid. Such salts include N-(2-aminophenyl)-4-(N-(pyridin-3-yl)methoxycarbonylaminomethyl)benzamide hydrochloride, N-(2-aminophenyl)-4-(N-(pyridin-3-yl) methoxycarbonylaminomethyl)benzamidehydrobromide, N-(2-aminophenyl)-4-(N-(pyridin-3-yl)methoxycarbonyl-aminomethyl)benzamide sulfate, N-(2-aminophenyl)-4-(N-(pyridin-3-yl)methoxycarbonylaminomethyl)benzamide phosphate, N-(2-aminophenyl)-4-(N-(pyridin-3-yl) methoxycarbonylaminomethyl)benzamide acetate, N-(2-aminophenyl)-4-(N-(pyridin-3-yl)methoxycarbonylamino-methyl)benzamide lactate, N-(2-aminophenyl)-4-(N-(pyridin-3-yl)methoxycarbonylaminomethyl)benzamide tartrate, N-(2-aminophenyl)-4-(N-(pyridin-3-yl) methoxycarbonylaminomethyl)benzamide malate, N-(2-aminophenyl)-4-(N-(pyridin-3-yl)methoxycarbonyl-aminomethyl)benzamide succinate, N-(2-aminophenyl)-4-(N-(pyridin-3-yl)methoxycarbonylaminomethyl)benzamide fumarate, N-(2-aminophenyl)-4-(N-(pyridin-3-yl) methoxycarbonylaminomethyl)benzamide maleate, N-(2-aminophenyl)-4-N-(pyridin-3-yl)methoxycarbonylamino-methyl)benzamide citrate, N-(2-aminophenyl)-4-(N-(pyridin-3-yl)methoxycarbonylaminomethyl)benzamide trifluoroacetate, N-(2-aminophenyl)-4-(N-(pyridin-3-yl) methoxycarbonylaminomethyl)benzamide p-toluenesul-fonate and N-(2-aminophenyl)-4-(N-(pyridin-3-yl) methoxycarbonylaminomethyl)benzamide methane-sulfonate, and others.

1D10 Antigen and Antibodies

The 1D10 antigen was originally identified as an epitope on the surface of malignant B lymphocytes (R. D. Gingrich et al., 1990, Identification and characterization of a new surface membrane antigen found predominantly on malignant B lymphocytes, Blood 75:2375–87).

Antibodies immunospecific for the 1D10 antigen have been developed (see for example, U.S. Pat. No. 6,129,914 to Weiner et al., issued Oct. 10, 2000) and can induce complement-mediated cytotoxicity, antibody-dependent cell cytotoxicity and/or apoptosis of cells expressing the 1D10 antigen (see for example, S. A. Kostelny et al., 2001, Humanization and characterization of the anti-HLA-DR antibody 1D10, Int. J. Cancer 93:556–65).

Various forms of an antibody immunospecific for 1D10 antigen may be used in practice of the methods of this invention. For example, the 1D10 antibody may be a full length antibody (e.g., having a human immunoglobulin constant region) or an antibody fragment (e.g. a F(ab')$_2$). The term "antibody" as used herein encompasses monoclonal antibodies (including full length monoclonal antibodies), polyclonal antibodies, multispecific antibodies (e.g., bispecific antibodies), and antibody fragments so long as they exhibit the desired biological activity of binding to 1D10 antigen. "Antibody fragments" comprise a portion of a full length antibody, generally the antigen binding or variable region thereof Examples of antibody fragments include Fab, Fab', F(ab')$_2$, and Fv fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The monoclonal antibodies to be used in accordance with the present invention may be made by the hybridoma method first described by G. Kohler & C. Milstein, 1975, Nature 256:495–7, or may be made by recombinant DNA methods (see, e.g., U.S. Pat. No. 4,816,567 to Cabilly et al., issued Mar. 28, 1989). The "monoclonal antibodies" may also be isolated from phage antibody libraries using the techniques described in Clackson et al., 1991, Nature 352:624–8 and Marks et al., 1991, J. Mol. Biol. 222:581–97, for example.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Single-chain Fv" or "sFv" antibody fragments comprise the VH and VL domains of antibody, wherein these domains are present in a single polypeptide chain. Generally, the Fv polypeptide further comprises a polypeptide linker between the VH and VL domains which enables the sFv to form the desired structure for antigen binding.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-polyacrylamide gel electrophoresis under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step In order to avoid potential immunogenicity of the monoclonal antibodies in human, the monoclonal antibodies that have the desired function are preferably humanized. "Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., 1986, Nature 321:522–5, Reichmann et al., 1988, Nature 332:323–9, and Presta, 1992, Curr. Op. Struct. Biol. 2:593–6.

Methods of making an 1D10 antibody, particularly a humanized form of the 1D10 antibody, are described in U.S. Pat. No. 6,129,914 to Weiner et al,. issued Oct. 10, 2000, the description of which is specifically incorporated herein by reference. Such antibodies are also available from, for example, Protein Design Labs, Inc., Fremont, Calif.

The preferred portion of the 1D10 antigen on B-CLL cells to which the 1D10 monoclonal antibody binds, or is immunospecific for, is a heterodimeric polypeptide which contains two proteins with a molecular weight of the alpha and beta chains being 32 kDa and 28 kDa, respectively. The proteins can be obtained by solubilizing cells expressing the antigen with detergent. Molecular weight determination is made by using iodinated cells and single dimension SDS-polyacrylamide gel electrophoresis analysis of an antibody precipitate obtained from extracts of the iodinated cells. The formation of one 1D10 antibody is discussed by Gingrich et al., 1990, Blood 75:2375–2387. Other antibodies having the same or similar binding specificity to 1D10 are screened by competition binding with 1D10 to the 28/32 kDa heterodimeric antigen. Numerous types of competitive binding assays are known, for example: solid phase direct or indirect radioimmunoassay (RIA), solid phase direct or indirect enzyme immunoassay (EIA), sandwich competition assay (see Stahli et al., 1983, Methods in Enzymology 9:242–53), solid phase direct biotin-avidin EIA (see Kirkland et al., 1986, J. Immunol. 137:3614–9), solid phase direct labeled assay, solid phase direct labeled sandwich assay (see Harlow & Lane, 1988, "Antibodies, A Laboratory Manual," Cold Spring Harbor Press); solid phase direct label RIA using I-125 label (see Morel et al., 1988, Molec. Immunol. 25:7–15), solid phase direct biotin-avidin EIA (Cheung et al., 1990, Virology 176:546–52); and direct labeled RIA (Moldenhauer et al., 1990, Scand. J. Immunol. 32:77–82). Typically, such an assay involves the use of cells bearing the 28/32 kDa antigen, an unlabelled test immunoglobulin and a labeled reference immunoglobulin (1D10). Competitive inhibition is measured by determining the amount of label bound to the cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

Pharmaceutical Compositions

The benzamide derivatives shown as structures I, II or III in the Summary of the Invention section of this application are preferably parts of pharmaceutical compositions intended for administration to a patient.

The benzamide derivatives, or the pharmaceutically acceptable salts thereof, may be prepared with generally used diluents, excipients, vehicles and additives such as filler, extender, binder, carrier, salt, moisturizing agent, disintegrator, disintegrator retarder, absorption promoters, adsorbent, glidant, buffering agent, preservative, dispersing agent, wetting agent, suspending agent, surfactant, lubricant and others. The benzamide derivatives or the pharmaceutically acceptable salts thereof may have a variety of dosage forms depending on their therapeutic purpose; typically tablet, pill, powder, solution, suspension, emulsion, granule, capsule, injection (e.g., solution, suspension) and suppository.

For preparing tablets, a variety of carriers well-known in the art may be used. Such a carrier includes excipients such as lactose, glucose, starch, calcium carbonate, hydrogenated vegetable oil, kaoline, crystalline cellulose and silicic acid; binders such as water, ethanol, propanol, simple syrup, glucose solution, starch solution, gelatin solution, carboxymethyl cellulose, shellac, methyl cellulose and polyvinyl pyrrolidone, powdered acacia, powdered tragacanth gum and gelatin; disintegrators such as calcium carmelose, agar, dried starch, sodium alginate, powdered agar, calcium carmelose, starch and lactose; disintegration retarders such as sucrose, cocoa butter and hydrogenated oil; absorption promoters such as quaternary ammonium base and sodium lauryl sulfate; moisturizing agents such as glycerin and starch; adsorbents such as starch, lactose, kaoline, bentonite, colloidal silicic acid; and glidants such as talc, stearates and polyethylene glycol. The tablet may be, if necessary, one coated with a common coating; for example, sugar-coated tablet, gelatin-coated tablet, enteric coated tablet, film-coated tablet, double-layer tablet and multilayer tablet.

Capsules may be prepared by blending an active ingredient with a variety of the above carriers as usual and filling the resulting blend into, for example, a hard or soft gelatin capsule or the like.

Injection, solution, emulsion and suspension forms of the benzamide derivatives or their pharmaceutically acceptable salts are sterilized and preferably isotonic with blood. Such forms may be prepared using diluents commonly used in the art; for example, water, ethanol, macrogol, propylene glycol, ethoxylated isostearyl alcohol, polyoxyisostearyl alcohol and polyoxyethylene sorbitan fatty acid esters. The pharmaceutical preparation may contain sodium chloride necessary to prepare an isotonic solution, glucose or glycerin, as well as usual solubilizers, buffers and soothing agents.

Compositions suitable for parenteral administration conveniently comprise a sterile, pyrogen-free, aqueous or oleaginous preparation of the benzamide derivatives which are preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa. The pharmaceutical compositions may conveniently be presented in unit dosage form and may be prepared by any of the methods well-known in the art of pharmacy.

Additionally, preparation of parenterally-acceptable solutions of the pharmaceutical composition, having due regard to pH, isotonicity, stability, and the like, is within the level of ordinary skill in the art of pharmacy and pharmacology. A preferred pharmaceutical composition for injection can contain, in addition to the vector, an isotonic vehicle such as Sodium Chloride Injection, Ringer's Injection, Dextrose Injection, Dextrose and Sodium Chloride Injection, Lactated Ringer's Injection, phosphate buffered saline (PBS), or other vehicle as known in the art. The pharmaceutical composition used in the methods of the present invention may also contain stabilizers, preservatives, buffers, antioxidants, or other additives known to those of skill in the art.

Suppository forms of the benzamide derivatives or their pharmaceutically acceptable salts may be prepared using a variety of well-known carriers; for example, semi-synthetic glyceride, cocoa butter, higher alcohols, higher alcohol esters and polyethylene glycol.

Furthermore, the composition may contain coloring agents, preservatives, perfumes, flavors, sweeteners and/or other drugs. The amount of the active ingredient in the composition may be, as appropriate, selected from a wide range with no limitations, and is generally about 1 to 70% by weight in the composition, preferably about 5 to 50% by weight.

The antibodies immunospecific for 1D10 are preferably parts of pharmaceutical compositions intended for administration to a patient. Pharmaceutical compositions comprising antibodies of the present invention are useful for parenteral administration, i.e., subcutaneously, intramuscularly and particularly, intravenously. The compositions for parenteral administration commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. The compositions may contain pharmaceutically-acceptable auxiliary substances as required to approximate physiological conditions such as pH adjusting and buffering agents, toxicity adjusting agents and the like, for example sodium acetate, sodium chloride, potassium chloride, calcium chloride and sodium lactate. The concentration of the antibodies in these formulations can vary widely, i.e., from less than about 0.01%, usually at least about 0.1% to as much as 5% by weight and will be selected primarily based on fluid volumes and viscosities in accordance with the particular mode of administration selected. A typical composition for intravenous infusion can be made up to contain 250 ml of sterile Ringer's solution, and 10 mg of antibody (see Remington's Pharmaceutical Sciences, Mack Publishing Co., Easton, Pa.).

Administration of the Pharmaceutical Compositions

An administration route of the benzamide derivatives or pharmaceutically acceptable salt thereof is not limited, and is selected depending on patient's age, sex, severity of disease and other conditions. For example, tablet, pill, solution, suspension, emulsion, granule and capsule may be orally administered (i.e., through the mouth); injection may be intravenously administered solely or in combination with a common infusion fluid such as glucose, amino acids and the like, or if necessary, intramuscularly, subcutaneously or intraperitoneally as a sole preparation. Suppository may be intrarectally administered. Advantageously, the benzamide agent or its pharmaceutically acceptable salt, may be administered orally.

A "biologically effective amount" as used herein in reference to the benzamide derivatives, means an amount of the benzamide derivative sufficient to decrease the viability of B-CLL cells from patients with B-CLL, induce apoptosis of B-CLL cells from patients with B-CLL or induce or increase expression of 1D10 antigen in B-CLL cells from patients with B-CLL. Preferably, biologically effective amounts of the benzamide derivatives ameliorate the pathological effects of B-CLL in patients with the disease. Ultimately, the dosage will be determined using clinical trials. Initially, the clinician will administer doses that have been derived from animal studies. The effective amount can be achieved by one administration of the composition. Alternatively, the effective amount is achieved by multiple administrations of the composition to the animal.

Dose of the benzamide derivative may be selected, depending on their dosage form, patient's age, sex and severity of disease, and other conditions, as appropriate, but the amount of the active ingredient may be generally about 0.0001 to 100 mg/kg a day. It is recommended that a unit dosage form may contain about 0.001 to 1000 mg of the active ingredient.

The invention further provides for administration of the benzamide derivatives and a pharmaceutically effective amount of one or more 1D10 antibodies, preferably humanized anti-1D10 monoclonal antibodies, to a patient suspected of or known to have B-CLL. While it is possible to administer these two agents in any order or simultaneously, it is preferred that the benzamide derivative is administered before the antibody.

The compositions containing the antibodies immunospecific for 1D10 antigen are generally administered therapeutically, meaning the compositions are administered to a patient known to have or suspected of having B-CLL. The compositions containing the antibodies are administered in biologically effective amounts, meaning an amount sufficient to completely or partially arrest the B-CLL disease and its complications. Amounts effective for this use will depend upon the severity of the condition and the general state of the patient's own immune system, but generally range from about 0.01 to about 100 mg of antibody per dose, with dosages of from 0.1 to 50 mg and 1 to 10 mg per patient being more commonly used. Single or multiple administrations on a daily, weekly or monthly schedule can be carried out with dose levels and pattern being selected by the treating physician.

In some methods of treatment, the benzamide derivatives or benzamide derivatives and 1D10 antibodies are administered in combination with other therapies such as chemotherapy, surgery, radiotherapy, photodynamic therapy, gene therapy, antisense therapy, enzyme prodrug therapy, immunotherapy, fusion toxin therapy, antiangiogenic therapy, or any other therapy for B-CLL or any combination of these therapies.

The duration of therapy with the pharmaceutical compositions used in the methods of the present invention will vary, depending on the unique characteristics of the pharmaceutical composition and the particular therapeutic effect to be achieved, the severity of the disease being treated and the condition and potential idiosyncratic response of each individual patient. Ultimately the attending physician will decide on the appropriate duration of therapy with the pharmaceutical composition used in the method of the present invention.

Preferably, the methods of treatment described herein result in the patient being cured of the B-CLL or going into remission from the B-CLL, staying in remission and becoming a long-term survivor. However, it is not necessary that curing or remission and long-term survival be the result of the inventive treatment. Any increase in the lifespan of the patient with the inventive treatment as compared to lifespan without the inventive treatment is a desirable goal. Alternatively, effects of the inventive treatment may be measured as an improvement in the quality of life of the patient or decrease in patient suffering, absent an increase in lifespan of the patient.

EXAMPLES

The invention may be better understood by reference to the following examples which serve to illustrate but not to limit the present invention.

Example 1

Patients and Isolation of Their Peripheral Blood Mononuclear Cells

B-CLL cells were obtained from patients previously diagnosed as having B-CLL. These patients had B-CLL as defined by B. D. Cheson et al., 1996, Blood 87:4990–7. All patients with B-CLL had been without prior therapy for B-CLL for a minimum of 2 months.

Peripheral blood mononuclear cells (PBMCs) were obtained from the B-CLL patients and were also obtained from healthy volunteers as controls. Peripheral blood was collected from the patients or volunteers using standard techniques (see for example, S. Bennett and S. N. Breit, 1994, Variables in the isolation and culture of human monocytes that are of particular relevance to studies of HIV, J. Leukoc. Biol. 56:236–40). PMBCs were isolated from the blood using standard density gradient centrifugation using Ficoll-Paque Plus (Pharmacia Biotech, Picsataway N.J.). After isolation, the PBMCs were washed in phosphate-buffered saline (PBS).

Such PBMC preparations comprised leukocytes, including T cells, B cells, monocytes and NK cells. PBMC preparations from B-CLL patients used in this study typically comprised 50–90% B-CLL cells compared to only a few percent of B cells in PBMC preparations from the healthy volunteers.

Example 2
$LC_{50}$ Determination of MS-275 for B-CLL Cells

In order to accurately represent the in vivo situation where drug is eliminated from the bloodstream, $1\times10^6$ PBMCs from B-CLL patients or healthy volunteers, isolated as described in Example 1, were incubated in various concentrations of MS-275 in RPMI 1640 with 10% heat-inactivated fetal bovine serum for 4, 24 or 96 hours at 37° C. in 96-well plates. Following incubation in MS-275, the cells were removed from media containing MS-275 and re-incubated in media without the drug. Cells that were incubated in drug for 4 hours were re-incubated in media without drug for 92 hours. Cells that were incubated in drug for 24 hours were re-incubated in media without drug for 72 hours. Cells that were incubated in drug for 96 hours were not re-incubated in media. Viability of the cells was then analyzed using the MTT assay. In this assay, cells are exposed to MTT [i.e., 3-(4,5-dimethylthiazol-2-yl)-2,5-diphenyltetrazolium bromide], which is taken into the cells and reduced by mitochondrial dehydrogenase to a purple formazan, a large molecule which is unable to pass through intact cell membranes, and therefore accumulates in healthy cells. The ability of cells to reduce MTT is an indication of mitochondrial integrity and activity, which is interpreted as a measure of viability. To use the MTT assay, MTT reagent was added and the cells were incubated for an additional 24 hours before washing and analysis of purple formazan formation by spectrophotometry in a Labsystems 96-well plate reader. Data were plotted and values were calculated using Graph-Pad software (San Diego, Calif.). The data for the B-CLL cells are shown in FIG. 1.

The results show that the $LC_{50}$ with 4 hours of drug incubation was 1.21 µM for B-CLL cells (FIG. 1A). In a separate experiment, the $LC_{50}$ with 4 hours of drug incubation was at least 21.1 µM for normal cells (i.e., PBMCs isolated from individuals without B-CLL). The results in FIG. 1B show that the $LC_{50}$ with a continuous 96 hour drug incubation was 0.509 µM for B-CLL cells. In a separate experiment, the $LC_{50}$ with a 96 hour continuous drug incubation was at least 4.75 µM for normal cells. These experiments were performed using cells from thirteen separate patients and four normal volunteers. These results demonstrated that MS-275 has significant and selective activity against B-CLL cells relative to normal cells.

Example 3
MS-275 Induced Histone Acetylation in CLL Cells

Figure 2:
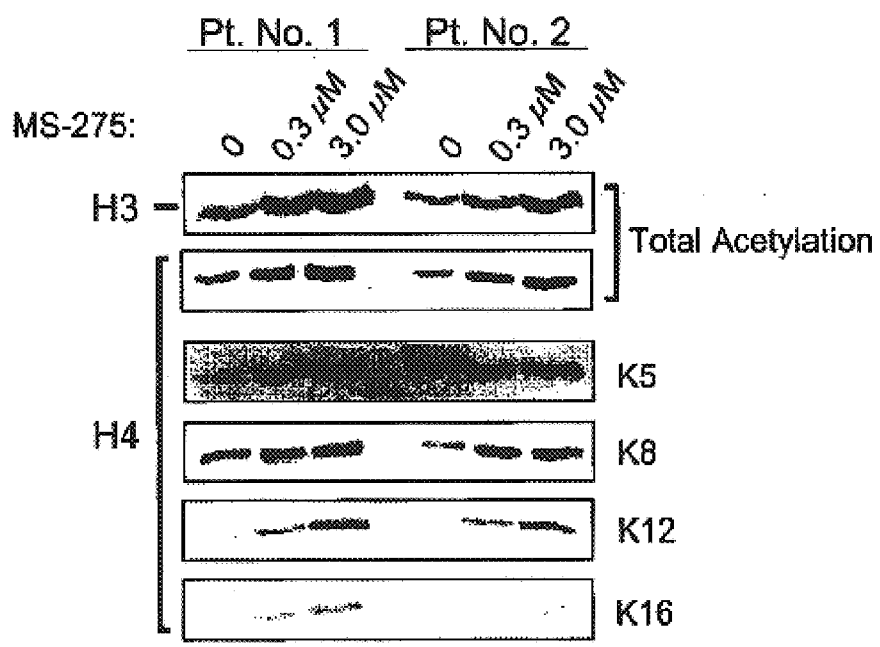
FIG. 2. MS-275 induced acetylation of histone proteins. PBMCs from two different B-CLL patients (Patient No. 1 and 2) were collected and incubated with 0, 0.3, or 3.0 μM MS-275 for 24 hours. Nuclear extracts were prepared from the cells and were separated by SDS-polyacrylamide gel electrophoresis before immunoblotting with antibodies immunospecific for acetylated forms of H3 or H4 histones. Coomassie blue staining was used to control for protein amount loaded onto the SDS polyacrylamide gels.

To determine if MS-275 caused inhibition of histone deacetylases, B-CLL cells, isolated as described in Example 1, were incubated with 0.3 or 3.0 µM of MS-275 for 24 hours and assessed for changes in histone acetylation by immunoblotting using antibodies immunospecific for acetylated H3 or H4 histones. Antibodies immunospecific for specific acetylated lysine residues at the N terminus of histone H4 (i.e., K5, K8, K12 and K16) were also used. For immunoblotting, whole cell lysates were prepared from the cells using standard procedures. Protein samples were separated along with molecular weight markers (BioRad) on 10 to 14% SDS-polyacrylamide gels. Proteins in the gels were transferred using a semidry apparatus (BioRad) onto nitrocellulose membranes (Schleicher and Schuell, Keene, N.H.). Gel loading equivalence was confirmed by Ponceau S stain (Sigma) of membranes and by probing with a monoclonal antibody for GAPDH. Blots were developed with chemiluminescent substrate (Pierce Super-Signal, Pierce Biotechnology, Rockford, Ill.) and autoradiography was performed with X-OMAT film (Kodak, Rochester, N.Y.). Protein bands were digitally quantified using a ChemiDoc instrument (BioRad). The immunoblot data are shown in FIG. 2. Quantification of these data are shown in Table 1 below.

TABLE 1

Fold Increase in Histone Acetylation
(Relative to Untreated) after 24 Hours of MS-275 Treatment.

| Patient No. | MS-275 Concentration | H3 Total | H4 Total | H4 K5 | H4 K8 | H4 K12 | H4 K16 |
|---|---|---|---|---|---|---|---|
| 1 | 0.3 µM | 1.3 | 2.4 | 2.7 | 1.6 | 4.4 | 3.7 |
|   | 3.0 µM | 2.3 | 3.9 | 8.9 | 1.9 | 15.8 | 9.1 |
| 2 | 0.3 µM | 1.5 | 3.8 | 2.6 | 4.4 | 5.1 | 3.1 |
|   | 3.0 µM | 3.1 | 5.2 | 4.5 | 4.8 | 10.3 | 4.7 |

The data show that there were increases in acetylation of both histones H3 and H4 due to MS-275. Generally, the data also show that acetylation of H4 lysines K5, K8, K12 and K16 also increased due to MS-275 treatment.

Example 4
MS-275-Induced Apoptosis in B-CLL Cells

Figure 3:
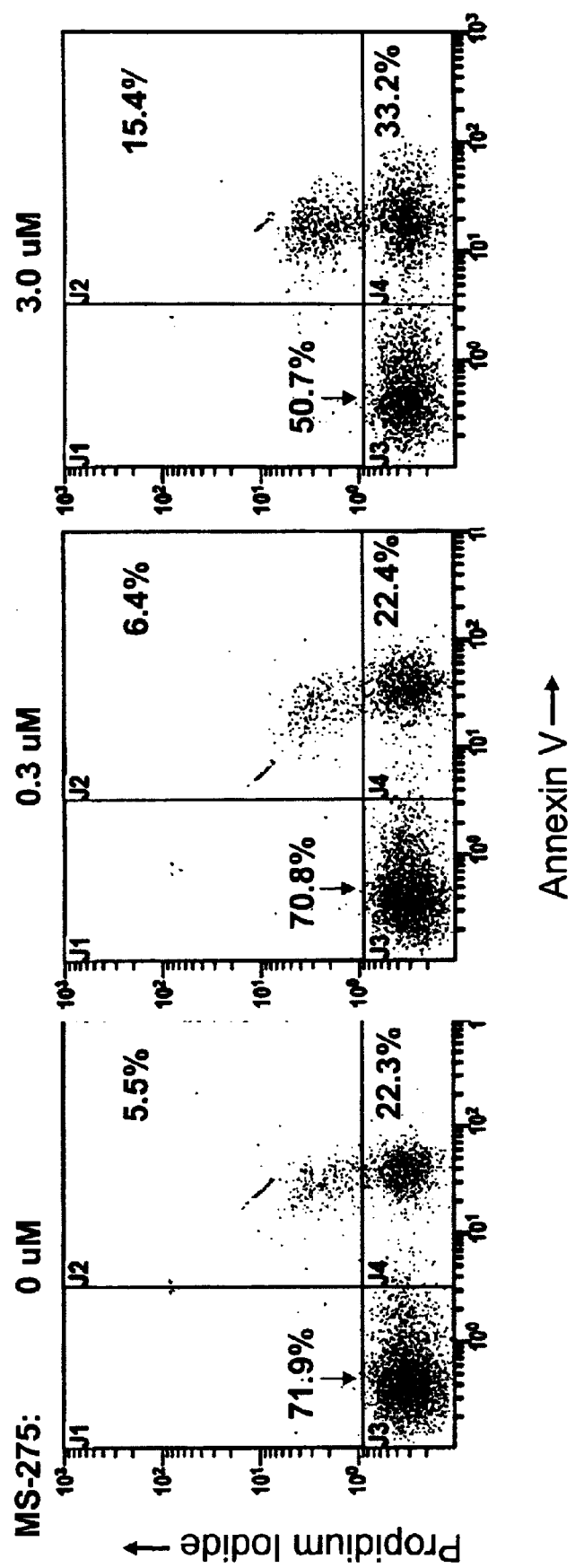
FIG. 3. MS-275 treatment of patient B-CLL cells resulted in apoptosis. B-CLL patient cells were incubated with 0, 0.3, or 3.0 μM MS-275 for 24 hours. Apoptosis was assessed by annexin V/propidium iodide flow cytometry.

To determine whether MS-275-treated B-CLL cells were undergoing apoptosis, an annexin V/propidium iodide flow cytometric assay was used to analyze the B-CLL cells, isolated as described in Example 1, from four different patients. Staining of cells for annexin V is an early indicator of initiation of apoptosis. Staining of cells with propidium iodide is an indicator that cells are no longer viable and, therefore, that apoptosis has actually occurred (i.e., integrity of cell membrane has been breached). To perform the assay, cells were exposed to various concentrations of MS-275 for 4 hours. Then, the cells were washed, resuspended in complete medium and incubated for 24 or 48 hours in absence of MS-275. At these times, cells were washed with PBS and resuspended in binding buffer containing annexin V-FITC and propidium iodide (BD Pharmingen, San Diego, Calif.). After 15 minutes of incubation in the dark at room temperature, apoptosis was assessed by flow cytometry on a Coulter EPICS-XL flow cytometer. The data (FIG. 3), from one representative patient, show that at 3.0 µM of MS-275, apoptosis was detected within 24 hours. The studies also showed that at 0.3 µM of MS-275, apoptosis was detected after 48 hours. The results were similar in the other three patients. These data show that MS-275 induced apoptosis in B-CLL cells.

In other studies it was shown that MS-275-induced apoptosis was inhibited by expression of the anti-apoptotic protein Bcl-2, indicating that MS-275 induces apoptosis via the intrinsic (mitochondrial) pathway.

Example 5
Pathway Utilized by CLL Cells Undergoing MS-275-Induced Apoptosis

Figure 4:
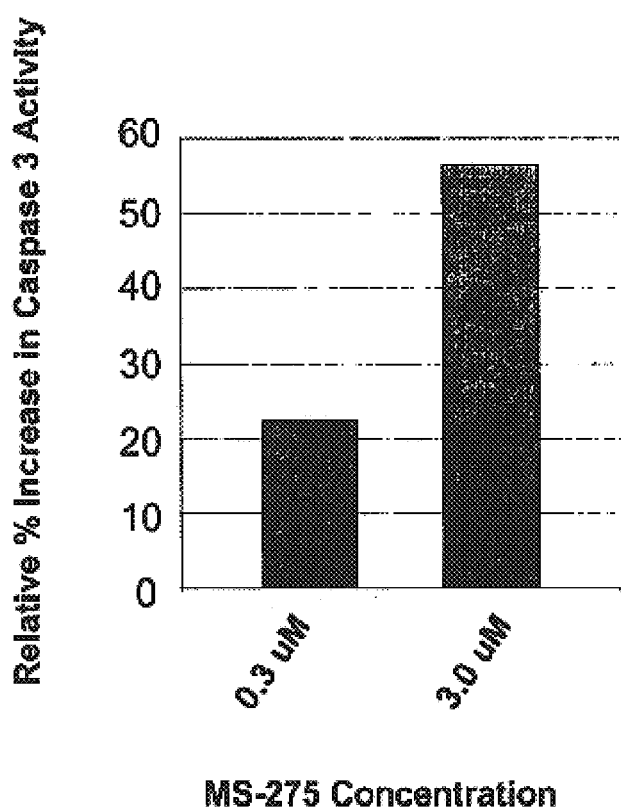
FIG. 4. MS-275 treatment of patient B-CLL cells resulted in cleavage of caspase 3. B-CLL patient cells were incubated with 0.3 or 3.0 μM MS-275 for 24 hours. At these time points, lysates were prepared from the cells and caspase 3 activity in the lysates was measured using a colorimetric assay.

To determine the role and identity of caspases involved in MS-275-induced apoptosis, B-CLL cells, isolated as described in Example 1, were treated with MS-275 and analyzed for caspase activation by colorimetric assay. Colorimetric assay kits from R&D Systems (Minneapolis, Minn.) were used as suggested by the manufacturer. As shown in FIG. 4, MS-275 induced activation of caspase 3. In other studies, it was found that caspases 8 and 9 were also activated to a lesser extent than caspase 3. Additional studies showed that the cleaved, activated forms of caspases 3, 8 and 9 were detected in B-CLL cells after treatment with MS-275. The activated caspase 3 was shown to cleave a known substrate, Poly(ADP-Ribose) Polymerase (i.e., PARP). Cleavage of the protein BID, a known substrate of caspase 8, was also shown.

Example 6

Increased Expression of 1D10 Antigen in B-CLL Cells by MS-275

Washed B-CLL cells, isolated as described in Example 1, from four different patients with B-CLL, were incubated at a concentration of $10^7$ cells per ml in the presence or absence of 3.0 µM MS-275 for 24 hours, before being immunofluorescently stained with either non-specific antibody (unable to specifically bind to the cells) or antibody immunospecific for 1D10 antigen. All cells were also stained with an antibody immunospecific for CD19 (recognizing B cells). The cells were analyzed by flow cytometry. The mean fluorescence intensity due to 1D10 antigen staining of CD19-positive cells was recorded. These results are shown in Table 2 below.

TABLE 2

1D10 Antigen Levels on B-CLL Cells after MS-275 Induction as Measured by Immunofluorescence Flow Cytometry

| | Patient No.[1] | | | |
|---|---|---|---|---|
| Cells | 1 | 2 | 3 | 4 |
| Staining control[2] | 1.19 (1) | 1.18 (1) | 1.98 (1) | 1.31 (1) |
| No drug control[3] | 69.45 (58) | 145.21 (123) | 2017.64 (1019) | 2424.39 (2232) |
| MS-275[4] | 104.11 (88) | 463.23 (393) | 6438.03 (3252) | 5446.76 (4158) |

[1]Patients 1–4 represent 4 different patients with B-CLL; the numbers in the table represent values for mean 1D10 fluorescence of the cells; the numbers in parenthesis are values normalized to the staining control for each patient.
[2]B-CLL cells, no drug treatment, were stained with a non-specific antibody.
[3]B-CLL cells, no drug treatment, were stained with antibody immunospecific for 1D10 antigen.
[4]B-CLL cells, MS-275 treatment, were stained with antibody immunospecific for 1D10 antigen.

The data show that B-CLL cells expressed relatively low levels of 1D10 antigen which were induced by MS-275 treatment.

What is claimed is:

1. A method for inducing apoptosis of B-CLL cells in a patient with B-CLL, comprising contacting the B-CLL cells with one or more anti-CLL agents, said agents comprising a benzamide derivative represented by the formula (I):

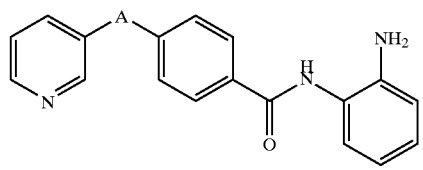

wherein A represents a structure shown by either of the formulas II, III or IV:

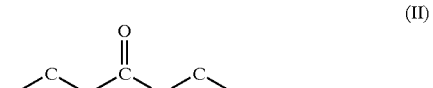

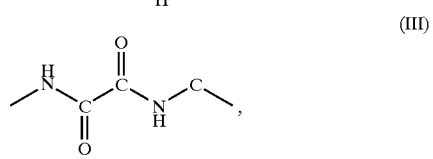

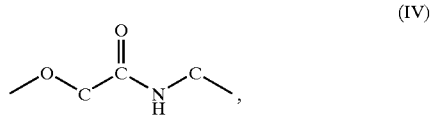

or a pharmaceutically acceptable salt thereof.

2. The method of claim 1 wherein the anti-CLL agent is represented by the formula (V):

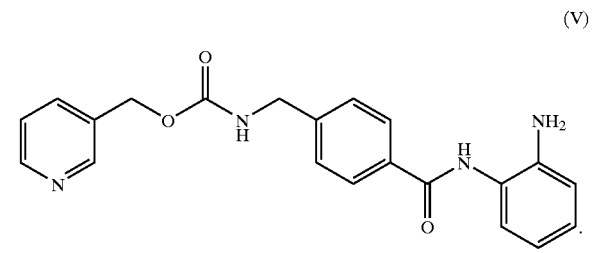

3. The method of claim 1 wherein the anti-CLL agent is represented by the formula (VI):

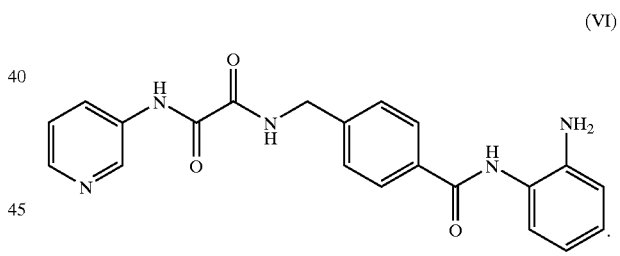

4. The method of claim 1 wherein the anti-CLL agent is represented by the formula (VII):

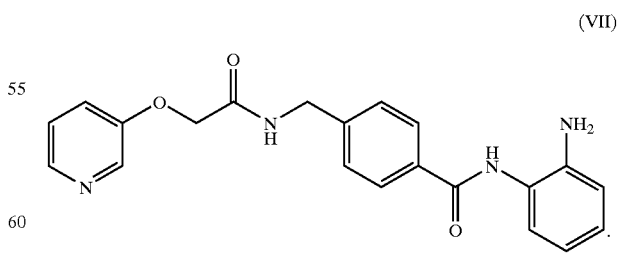

5. A method for increasing expression of 1D10 antigen in B-CLL cells in a patient with B-CLL, comprising contacting the B-CLL cells with one or more benzamide derivatives represented by the formula (I):

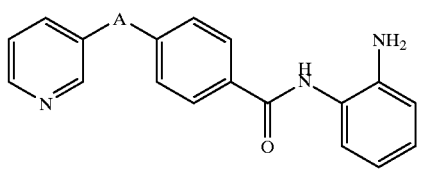
(I)

wherein A represents a structure shown by either of the formulas II, III or IV:

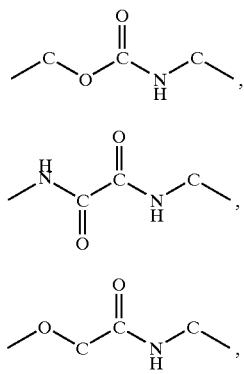

(II)

(III)

(IV)

or a pharmaceutically acceptable salt thereof.

6. The method of claim 5 wherein the benzamide derivative is represented by the formula (V):

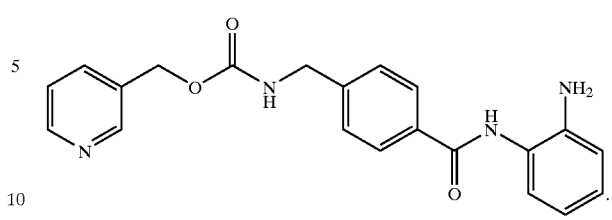
(V)

7. The method of claim 5 wherein the benzamide derivative is represented by the formula (VI):

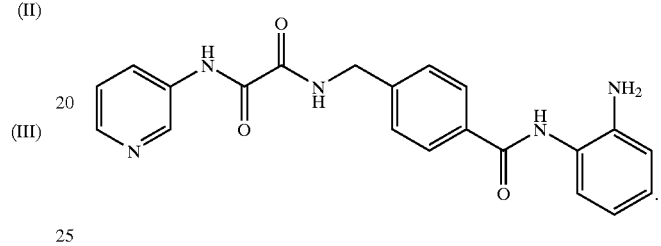
(VI)

8. The method of claim 5 wherein the benzamide derivative is represented by the formula (VII):

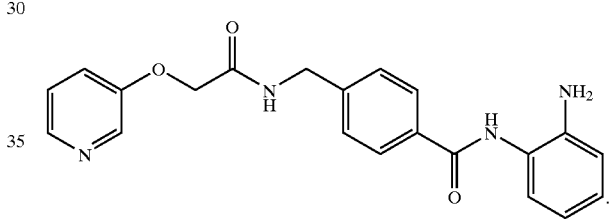
(VII)

* * * * *